United States Patent [19]
Schlesinger et al.

[11] Patent Number: 5,763,480
[45] Date of Patent: Jun. 9, 1998

[54] INHIBITORS OF CELL-MEDICATED DISORDERS

[75] Inventors: Paul H. Schlesinger; Steven L. Teitelbaum, both of University City, Mo.; Harry C. Blair, Mountain Brook, Ala.

[73] Assignee: The Jewish Hospital of St. Louis, St. Louis, Mo.

[21] Appl. No.: 196,293

[22] Filed: Feb. 14, 1994

[51] Int. Cl.$^6$ ............................................. A61K 31/28
[52] U.S. Cl. ..................... 514/476; 514/491; 514/492; 424/650
[58] Field of Search ................................ 514/476, 491, 514/492; 424/650

[56] References Cited

U.S. PATENT DOCUMENTS

| | | | |
|---|---|---|---|
| 4,551,431 | 11/1985 | Pierce | 424/650 |
| 4,591,506 | 5/1986 | Bonadis | 424/650 |
| 4,686,104 | 8/1987 | Bockman et al. | 514/492 |

OTHER PUBLICATIONS

Apseloff et al., "Long–Term Effects of Gallium Nitrate in Patients with Paget's Disease of Bone," *J. Bone Min. Res.*, 7, 1240 (1992).

Blair et al., "The Mechanism of Osteoclast Acidification," in *Biology and Physiology Of The Osteoclast* (Rifkin et al., eds.), Chapter 13, 259–286 (CRC Press, Boca Raton, FL, 1992).

Blair et al., "Reversible Inhibition of Osteoclastic Activity by Bone–Bound Gallium (III)," *J. Cell. Biochem.*, 48, 401–410 (1992).

Blair et al., "Passive Chloride Permeability Charge Coupled to H$^+$ATPase of Avian Osteoclast Ruffled Membrane," *Am. J. Physiol.*, 260, C1315–C1324 (1991).

Blair et al., "Purification of a Stilbene Sensitive Chloride Channel and Reconstitution of Chloride Conductivity into Phospholipid Vesicles," *Biochem. Biophys. Res. Com.*, 171, 920–925 (1990).

Blair et al., "Osteoclastic Bone Resorption by a Polarized Vacuolar Proton Pump," *Science*, 245, 855–857 (1989).

Blair et al., "Isolated Osteoclasts Resorb the Organic and Inorganic Components of Bone," *J. Cell Biol.*, 102, 1164–1172 (1986).

Blixt et al., "Equilibria and Dynamics of Tl(edta)X$^{2-}$ Complexes (X=Halide, Pseudohalide) Studied by Multinuclear NMR," *Inorg. Chem.*, 31, 5288–5297 (1992).

Carano et al., "Bisphosphonates Directly Inhibit the Bone Resorption Activity of Isolated Avian Osteoclasts in vitro," *J. Clin. Invest.*, 85, 456–461 (1990).

Cuppoletti et al., "The Lysosomal H$^+$ Pump: 8–azido–ATP Inhibition and the Role of Chloride in H$^+$ Transport," *Biochim. Biophys. Acta*, 899, 276–284 (1987).

Douglas et al., "Coordination Chemistry of Hexadentate EDTA–type ligands with M(III) Ions," *Coordination Chemistry Reviews*, 128 139–165, 1993).

Forgac, "Structure and Function of Vacuolar Class of ATP–Driven Proton Pumps,"*Physiol. Reviews*, 69, 765–796 (1989).

Gay, "Osteoclast Ultrastructure and Enzyme Histochemistry: Functional Implications," in *Biology and Physiology Of The Osteoclast*(Rifkin et al., eds.), Chapter 6, 129–150 (CRC Press, Boca Raton, FL, 1992).

Glickman et al., "Golgi Membranes Contain an Electrogenic H$^+$ Pump in Parallel to a Chloride Conductance," *J. Cell Biol.*, 97, 1303–1308 (1983).

Jaeger et al., "Animal Model of Primary Hyperparathyroidism," *Am. J. Physiol.*, 252, E790–E798 (1987).

Matovic et al., "The Effects of Gallium Nitrate in Patients with Paget's Disease of the Bone," *J. Bone Min. Res.*, 7, S288 (1992).

Rupich et al., "Lateral Dual–Energy Radiography: Artifact Error from Rib and Pelvic Bone," *J. Bone Miner. Res.*, 7, 97–100 (1992).

Schlesinger et al., "Bisphosphonates," in *Biology and Physiology Of The Osteoclast* (Rifkin et al., eds.), Chapter 18, 397–417 (CRC Press, Boca Raton, FL, 1992).

Sly, "Carbonic Anhydrase II Deficiency Syndrome," in *The Carbonic Anhydrases* (Dodgson, et al., eds.), 193–193 (1991).

Teti et al., "Cytoplasmic pH Regulation and Chloride/ Bicarbonate Exchange in Avian Osteoclasts," *J. Clin. Investigation*, 83, 227–233 (1989).

Thirwell et al., "Open Randomized Dose–Finding Study of Gallium Nitrate Administered Intravenously in Malignant Hypercalcemia," *J. Bone Min. Res.*, 7, S296 (1992).

*Primary Examiner*—James H. Reamer
*Attorney, Agent, or Firm*—Senniger, Powers, Leavitt & Roedel

[57] ABSTRACT

The present invention provides a method for blocking a cellular proton pump that comprises contacting a cell with a cellular proton pump-blocking effective quantity of In-EDTA or Tl-EDTA. The present invention also provides a method of treating or preventing cell-mediated disorders in a vertebrate animal by administering In-EDTA or Tl-EDTA to the vertebrate animal, as well as a method for stopping the cellular proton pump-blocking effect of Group IIIa metals such as Ga, In, and Tl, through use of suitable chelating agents. Suitable compositions for use in the aforementioned methods are provided as well.

12 Claims, 3 Drawing Sheets

1

INHIBITORS OF CELL-MEDICATED DISORDERS

This invention was made with government support under NIH Grant DEO 5413-13 and AR32788-09 by the National Institute of Health. The government has certain rights in the invention.

FIELD OF THE INVENTION

This invention relates to products and methods useful for the blocking of membrane function in animal cells. This invention further relates to the treatment or prevention of certain cell-mediated disorders in vertebrate animals, including osteoporosis, hypercalcemia, neoplastic bone resorption, and certain inflammatory responses.

BACKGROUND OF THE INVENTION

Certain disease states found in the skeletons of terrestrial animals result from the inappropriate activities of an animal's cells. For example, certain disorders of calcium metabolism, such as osteoporosis and hypercalcemia, and certain immunological syndromes, resulting in inflammatory responses, are mediated, respectively, by osteoclasts and various leukocytes (including macrophages), respectively employing the $H^+$-ATPases of these cells' membranes.

During a lifetime, the skeleton is remodeled many times in a continuous process. This metabolism is required to maintain normal physiologic processes, including growth, maintenance of a physically strong skeleton, and fulfillment of the skeleton's metabolic roles as a repository of calcium, base equivalents, and phosphate. Bone metabolism is mediated in part by the counteracting activities of two types of cells: (1) osteoblasts, which function to form bone tissue (and become osteocytes upon having done so); and (2) osteoclasts, which function to resorb bone tissue. The appropriate balance of the activities of osteoblasts and osteoclasts maintains the structural integrity and proper functioning of the skeleton in spite of continuous metabolism. Common maladies that result from an imbalance of the activities of these cell types are osteoporosis and hypercalcemia.

The regulation of continuous bone formation and resorption is closely controlled and necessarily coupled, but by as yet unknown mechanisms. Because these aspects of bone metabolism compete, their balance is essential to health. An abnormality in one aspect, perhaps due to an uncoupling of a regulatory mechanism, ultimately leads to major disruption in structural or metabolic functions, and the need for therapeutic intervention. The *Primer On The Metabolic Bone Disease And Disorders Of Mineral Metabolism* (Murray J. Favus et al., eds., 1993) contains a collection of articles that presents a wide array of information regarding bone metabolism and its disorders.

The skeleton is the repository of almost all of the body's calcium. It is the only accessible source of significant amounts of calcium available to fasting, land-living vertebrates. Intracellular free calcium concentration is regulated carefully to range between $10^{-8}$ and $10^{-9}$ M. In fact, induced changes in intracellular calcium concentration in this range play a central part in cellular regulation and control. Maintenance of extracellular calcium concentration at approximately 1.5 mM is, in turn, necessary for the maintenance of appropriate intracellular calcium concentrations.

Use of calcium as a major mediator of intracellular signals has been, for the higher vertebrates, particularly advantageous because of the availability of extensive extracellular reservoirs (i.e., the skeleton) of this crucial ion. The use of calcium as an intracellular signal, however, requires stringent regulation of the intracellular concentrations and protection from extracellular calcium concentrations that are present across the plasma membrane at concentrations in excess of four orders of magnitude higher than intracellular levels. Additionally, the immense solid calcium salt reservoirs of the skeleton are both a threat and a resource to the regulation of intracellular calcium by the cellular membranes.

There must be conservation of calcium stores, because the use of calcium, in its role as a signalling ion, and especially in systemic pH regulation, is necessarily balanced against the physical integrity of the skeleton. Therefore, any attempt to treat metabolic bone disease by influencing calcium metabolism through mass action or by dramatic hormone-induced shifts would certainly be difficult and potentially dangerous. An appreciation of the underlying biochemistry of any aspect of bone metabolism that is to be manipulated in treating a metabolic bone disease is critical.

For land-living vertebrates, the skeleton is a reservoir of both calcium and alkaline equivalents. This phenomenon can be demonstrated in situations involving calcium restriction and system acidosis, where removal of skeletal mineral can be extensive. As a reservoir, the skeleton plays a major role in the body's homeostasis of calcium and pH, which are both essential for normal cellular function. It has been known for some time that the regulation of intracellular and systemic pH within a restricted range is required for good health. More recently, the role of calcium as an intracellular signal mediator has been described. Bone, as the major reservoir for both of these roles of calcium, is impacted significantly by the regulation of each.

In addition, bone is a specialized connective tissue that is the supporting structural element for mammals. If the structural integrity of the skeleton is compromised due to disease or deficiency, a serious health threat immediately follows. Therefore, the successful regulation of bone metabolism is critical for both systemic homeostasis and for structural stability. Consequently, attempts to manipulate bone metabolism pharmacologically must be carefully considered.

In particular, bone consists of the specialized bone cells identified above (which comprise about 2% of the total bone volume) and an extensive extracellular matrix comprising bone mineral (essentially hydroxyapatite, which is designated chemically as $Ca_{10}(PO_4)_6(OH)_2$, and collagen. Osteoclasts resorb bone by attaching to the bone matrix surface and producing a localized acid environment on the bone surface that requires the secretion of acid that is equal to 1.5 times the calcium solubilized from bone mineral. This process has been elucidated and reviewed by Blair and Schlesinger in "The Mechanism Of Osteoclast Acidification," in *Biology And Physiology Of The Osteoclast* (B. R. Rifkin and C. V. Gay, eds., 1992) at pages 259–286. Because the osteoclast is the bone-resorbing cell, the control of excessive bone loss has been focused on the regulation of osteoclast activity. Bone loss is associated with a number of diseases and conditions, including osteoporosis, bone resorption in neoplastic metastases that produce hypercalcemia, rheumatoid arthritis, and treatment situations involving, for example, the administration of glucocorticoids.

Upon adherence of the osteoclast to bone matrix, at minimum, three ion transport functions and carbonic anhydrase are used by this cell to establish and maintain the observed localized secretion of sufficient protons. This coordinated activity causes the local area between the osteoclast cell membrane and the bone surface to become acidic enough to result in dissolution of the underlying bone (Blair and Schlesinger, supra). The energy for proton transport is provided by a $H^+$-dependent ATPase that is located in the ruffled membrane of the osteoclast. This ATPase is immunologically (Blair et al., *Science*, 245, 855–857 (1989)) and functionally (Blair et al., *Am. J. Physiol.*, 260, C1315–C1324 (1991)) similar to the endosomal proton pump. As in acid intracellular vesicles (Forgac, *Physiol. Review*, 69, 765–796 (1989); Glickman et al., *J. Cell Biol.*, 97, 1303–1308 (1983); Cuppoletti et al., *Biochimica et Biophisica Acta*, 899, 276–284 (1987); Blair et al., supra), this electrogenic pump functions in parallel with a chloride ion channel, also located in the ruffled membrane. The functioning of the chloride channel is essential, as evidenced by a cessation of the proton pump-mediated transport of protons when the complementary anion (chloride) transport is reduced (Blair et al., supra; Blair & Schlesinger, *Biochem. Biophys. Res. Com.*, 171, 920–925 (1990)).

This net HCl secretion would result in intracellular alkalinization and chloride depletion, except that an active intracellular carbonic anhydrase (Gay, in *Biology and Physiology of The Osteoclast* (B. R. Rifkin and C. V. Gay, eds., 1992) at pages 129–152; Sly, in *The Carbonic Anhydrases* (S. Dodgson, et al., eds., 1991) at pages 183–193) produces carbonic acid, $H^+$, and bicarbonate, thereby correcting the proton loss. Finally, a basolateral $Na^+$-independent $Cl^-/HCO_3^-$ exchange exports the alkaline equivalents from the cell, thereby restoring appropriate intracellular chloride ion and pH levels (Teti et al., *J. Clin. Investigation*, 83, 227–233 (1989)).

As mentioned above, loss of bone mass due to unbalanced osteoclast-osteoblast activity may be associated with a wide range of diseases, including osteoporosis in its many manifestations and hypercalcemia, diseases that occur in millions of patients in the United States alone. Osteoporosis is commonly diagnosed as the cause of a bone fracture in an individual of normal serum calcium levels who experienced no obvious stress on the bone prior to the fracture. Osteoporosis is most common in post-menopausal females, but may occur in pre-menopausal females or, more rarely, in males. Abnormal bone loss also may occur in patients afflicted with hypercalcemia, a disease named for its characteristic high concentrations of calcium in the blood. Hypercalcemia, usually associated with malignant cancer or primary hyperparathyroidism, can lead to kidney failure, coma, and death. A hypercalcemic patient can experience progressive bone erosion, ongoing excessive pain, and fractures.

The ability to regulate bone mass and quality without significantly altering non-bone calcium and phosphate regulation is the goal of treatment of most types of chronic metabolic bone disease, such as osteoporosis and hypercalcemia of malignancy. The intimate interrelation between bone metabolism and calcium ion concentration makes this goal difficult to achieve.

A strategy for the successful regulation of bone metabolism is based on the effective and reversible inhibition of the HCl-secretion mechanism of bone dissolution by osteoclasts. Because the osteoclasts are essentially fully differentiated cells, one approach for such inhibition is to suppress their development from stem cells, or to destroy the stem cells. However, until more is known about differentiation and neoplastic transformation, particularly with regard to this cell type, the former, inhibition of development, may be a dangerous route and the latter, elimination of the stem cell line, would likely preclude reversal of over-treatment.

Another approach employed in the past incorporated the use of the Group IIIa metal gallium (Ga) as gallium nitrate, which does reduce excessive loss of bone calcium in humans. This effect of gallium compounds is disclosed in U.S. Pat. Nos. 4,529,593 and 4,704,277. However, this use of such gallium compounds has been shown to have only limited utility because of associated adverse effects, such as anemia, nausea and vomiting, and renal toxicity. Osteoblasts, the cells responsible for increasing bone mass, appear to suffer adverse effects from the existing gallium compound treatments as well. See Thirwell et al., *J. Bone Min. Res.*, 7, S296 (1992); Apseloff et al., *J. Bone Min. Res.*, 7, 1240 (1992); Matovic and Austin, *J. Bone Min. Res.*, 7, S288 (1992). Aluminum (Al), another Group IIIa metal, has been noted in accidental poisoning cases to inhibit bone resorption.

Over the past thirty years, the use of bisphosphonates has been noted to effect a specific reduction of bone resorption. Bisphosphonates include two phosphorous atoms bound to a common carbon atom. Bisphosphonates were the first artificial, end organ-specific drugs for bone disease. Unfortunately, the experience in the late 1960's with the first bisphosphonate used, etidronate, did not fulfill the high expectations for this therapy. While etidronate proved to be an effective inhibitor of bone resorption and a useful treatment of Paget's disease, myositis ossificans, osteoporosis, and other bone demineralization diseases, the use of etidronate also resulted in impaired mineralization and thus, paradoxically, increased bone fragility.

More recently, other bisphosphonate compounds have been developed that are also powerful inhibitors of bone resorption, but which have lesser effects on mineralization. One of these, clodronate, was tested extensively in the late 1970's and early 1980's, and was found to be effective not only in Paget's disease, but also in the treatment of hypercalcemia and osteolytic bone disease. Unfortunately, long-term clodronate therapy became associated with development of acute leukemia. See Schlesinger and Blair, "Bisphosphonates," in *Biology and Physiology of the Osteoclast* (B. R. Rifkin and C. V. Gay, eds., 1992) at pages 397–417.

The mechanism of action of bisphosphonates has been studied by Careno et al., *J. Clin. Invest.*, 85, 456–461 (1990). Bisphosphonate impedes the bone resorption activity of osteoclasts in a dose-dependent manner. The relative specificity of effect on osteoclasts results from the fact that bone matrix serves as a sink for bisphosphonates. Delivery of the drug to osteoclasts, which are found on the surface of metabolically active bone, is based on local high concentration of the drug. However, bisphosphonates may have other effects, as noted above, such that use of bisphosphonate therapy presents considerable risk of deleterious side-effects to patients.

In addition to the aforementioned calcium metabolism diseases, other conditions can result in significant bone loss. For example, therapy with corticosteroids can result in bone loss such that the discontinuation of therapy is required. Also, chronic inflammation due to rheumatoid arthritis can cause local bone destruction and permanent disability and deformity. The bone loss in both of these conditions may be caused by either local or systemic unbalanced osteoclast-osteoblast activities. There is no effective and sufficiently specific treatment available today for these conditions, both of which appear to be inflammatory responses affecting bones that involve macrophages.

The ability of gallium (III) compounds and bisphosphonates to ameliorate disorders of bone metabolism, possibly including those secondary to inflammation- and corticosteroid-induced bone loss, is probably a consequence of the characteristic of the highly charged bone matrix to bind avidly many charged and hydrophilic compounds. In a sense, bone behaves as an ion exchange medium, binding such compounds to its surface. See Carano et al., supra; Blair et al., *J. Cell. Biochem.*, 48, 401–410 (1992). Unfortunately, neither bisphosphonates nor Ga(III) compounds appear to remain at the bone surface, perhaps being released by action of the osteoclasts themselves, and appear to cause general toxicity upon release. An approach in which the effect is limited to the bone surface only, and in which the effect is reversible, would be desirable.

In view of the history and mechanism of bisphosphonate and gallium (III) nitrate therapies for calcium metabolism disorders, and the lack of effective treatment for inflammatory responses affecting bone, another approach to reducing the bone resorption activity of the osteoclasts and inflammatory response of macrophages is needed.

SUMMARY OF THE INVENTION

It has now been discovered that compositions comprising a chelating agent and certain metals are capable of blocking the proton pump on the surface of the osteoclast. In addition to in vitro applications, these compositions can be used to control certain cell-mediated disorders of bone metabolism that involve unbalanced osteoclast-mediated bone resorption and macrophage-mediated inflammation, for example. Additionally, it has been discovered that the deleterious effects of the gallium nitrate-type therapy or overdoses of Group IIIa metals can be controlled or stopped by the administration of a suitable chelating agent.

Accordingly, the present invention provides a method for blocking a cellular proton pump or for treatment or prevention of cell-mediated disorders in vertebrate animals that comprises contacting a cell in vivo or in vitro with a cellular proton pump-blocking-effective quantity of In-EDTA or Tl-EDTA. The present invention also provides a method for reversal of that inhibition of a cellular proton pump. This employs contacting a cell with a cellular proton pump-blocking-effective quantity of a Group IIIa metal or salt followed by subsequently contacting said cell with a Group IIIa metal chelating agent that reverses the pump inhibition by sequestering the metal in an inactive complex. The present invention further provides a method for the treatment of toxic quantities of Group IIIa metals comprising administration of at least one chelating agent selected from the group consisting of EGTA, CDTA, and DPTA. The present invention yet further provides compositions used in the aforementioned methods, comprising certain Group IIIa metals and certain chelating agents.

These and other features and advantages of the invention will be more readily apparent upon reading the following detailed description of the invention and upon reference to the accompanying drawings, all of which are given by way of illustration only, and are not limitative of the present invention.

DETAILED DESCRIPTION OF THE INVENTION

The following detailed description of the invention is provided to aid those skilled in the art in practicing the present invention, but should not be construed to limit the present invention, as modifications and variations in the embodiments herein discussed may be made by those of ordinary skill in the art without departing from the spirit or scope of the present inventive discovery.

The present invention provides compositions and methods that inhibit the cellular proton pump in a selective manner. Specifically, the present invention provides a method for blocking a cellular proton pump that comprises contacting a cell with a cellular proton pump-blocking-effective quantity of the metal-chelate complex In-EDTA or Tl-EDTA, wherein In is indium, Tl is thallium, and EDTA is ethylenediaminetetraacetic acid. Any cell may be considered an appropriate subject for the inventive method, whether in vitro or in vivo, including but not limited to osteoclasts, macrophages, neutrophils, lymphocytes and others. Preferred subjects for this method are osteoclasts and macrophages. More preferred subjects are osteoclasts.

The cells may be contacted with the In-EDTA or Tl-EDTA by any suitable means. For example, these compounds may be added to a culture medium in which the cells are cultured in vitro. These compounds may also be administered in vivo to a vertebrate animal.

The present inventive method also contemplates the subsequent contact of the cell with an uncomplexed chelating agent that reverses the cellular proton pump-blocking-effect of the In-EDTA or Tl-EDTA, as may be desirable, for example, in the case of accidental or intentional administration of an overdose amount of an invention compound. Any such suitable chelating agent that will form an inactive complex with the metal may be so used. Examples of suitable chelating agents include ethylene glycol bis (o-aminoethyl ether) N,N,N',N'-tetraacetic acid (EGTA), trans-1,2-diaminocyclohexane-N,N,N',N'-tetraacetic acid (CDTA), and diethylenetriaminepentaacetic acid (DPTA).

Figure 1:
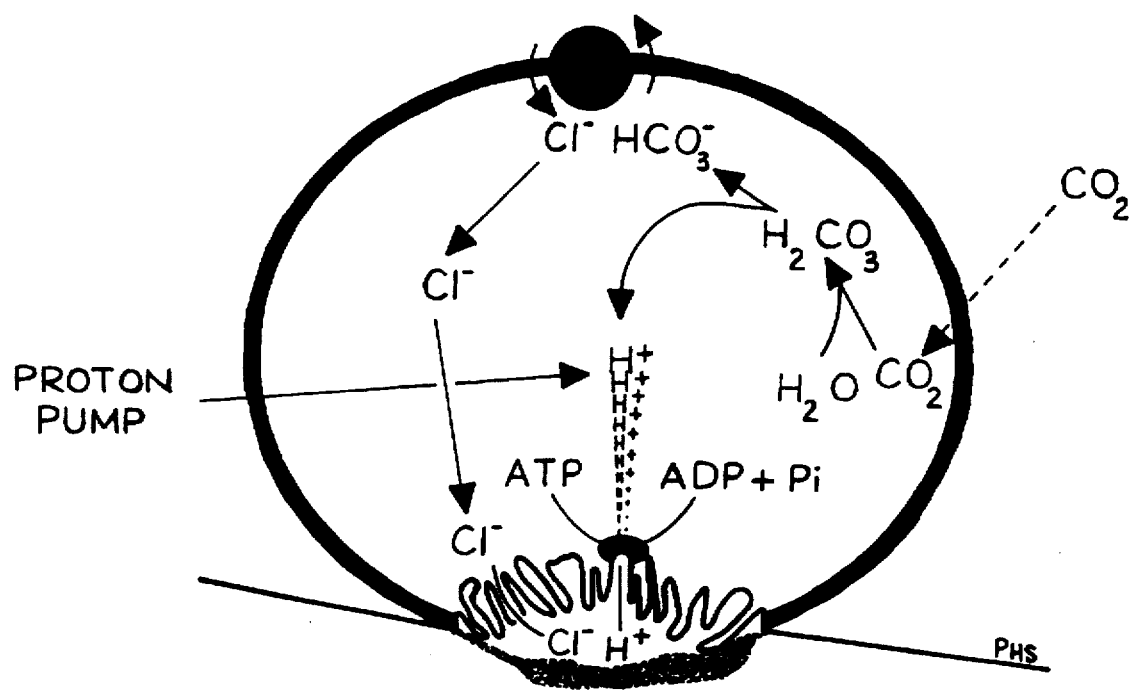
FIG. 1 is a schematic of ion transport supporting proton secretion through the ruffled membrane of an osteoclast.

The cellular proton pump has central importance in the activity of osteoclasts, where its role, as depicted in FIG. 1, is coordinated with two other ion transport mechanisms and carbonic anhydrase. Controlling this proton pump provides a means to effect selectively bone dissolution, which, in addition to providing the basis for the utility of the present inventive methods and compositions used therein, improves on existing therapy of calcium metabolism disorders. Such calcium disorders include osteoporosis, Paget's disease, hypercalcemia, and others. Using the present invention, the non-bone calcium ion ($Ca^{++}$) regulatory mechanisms are not altered, because the natural feedback mechanisms of serum ion homeostasis are not disrupted and compensate in the normal way for the altered rate of bone deposition or formation caused by the present invention. Thus, the only noticeable effect is on the skeleton. The effective delivery to the bone of substances that reduce osteoclastic bone resorption processes provides the desired selectivity of therapy. Moreover, the present invention, by inhibiting the cellular proton pump, can be used to treat other cell-mediated disorders, such as macrophage-mediated inflammatory responses and bone destruction, as occurs in rheumatoid arthritis and metastatic disease, for example.

The present invention provides a method for the treatment or prevention of bone resorption disorders in a vertebrate animal afflicted with or at risk of increased bone resorption comprising administering a therapeutically- or prophylactically-effective quantity of In-EDTA, or Tl-EDTA. Preferred vertebrate animals that may find this method useful include humans and domestic animals. A chelating agent that stops the therapeutic or prophylactic effect of the In-EDTA or Tl-EDTA, i.e., that stops the cellular proton pump-blocking effect of those compounds, may be administered subsequently to stop the initiated effect. Such suitable chelating agents include those that form hexadentate complexes with a group IIIa metal, as previously discussed, and, specifically, the following that have been demonstrated and disclosed herein: EGTA for gallium (III) (hereinafter "Ga(III)"); and CDTA or DPTA for In(III) and Tl(III). Cell-mediated disorders that may be treated by this inventive method include those that affect calcium metabolism, such as osteoporosis, Paget's disease, or hypercalcemia, or those that affect bone resorption and are due to inflammation and neoplastic disease.

The present invention also provides a sequential method for blocking and unblocking a cellular proton pump that comprises contacting a cell with a cellular proton pump-blocking-effective quantity of a Group IIIa metal followed by contacting the cell with a sequestering-effective quantity of a chelating agent that stops said cellular proton pump-blocking effect. The present sequential contacting method may be effected in vitro by culturing the cell with the Group IIIa metal, preferably as a suitable salt, e.g., a nitrate salt, followed by the chelating agent, or in vivo by administering to an individual the Group IIIa metal followed by the chelating agent. The Group IIIa metal may be any or all of the following elements: aluminum (Al), Ga, Tl, and In. The chelating agent for in vivo administration may be administered by any suitable means, e.g., by oral, sublingual, vaginal, rectal, parenteral, or transdermal means. Such use of the chelating agent is desirable, for example, in the case of accidental or intentional administration of an overdose amount of the Group IIIa metal.

The chelating agent used in the present inventive sequential method may be any suitable chelating agent, preferably those having at least six coordinating sites, such as EDTA, EGTA, CDTA, or DPTA. Preferred chelating agents are EDTA and CDTA. EDTA, however, is not a suitable chelating agent for stopping the effect when the metal is Tl or In. The inhibitory chelating agent is most preferably EDTA, however, when the metal is Al or Ga. The cell upon which the present inventive method acts may be any proton pump-containing cell, including but not restricted to osteoclasts or macrophages. Preferably, the present invention is used to treat vertebrate animal cells, including osteoclasts and macrophages.

The present invention is also embodied as a method for the treatment or prevention of cell-mediated disorders in a vertebrate animal, preferably humans, comprising administering to a vertebrate animal afflicted with or at risk to a cell-mediated disorder a therapeutically- or prophylactically-effective quantity of a Group IIIa metal followed at an appropriate time by a neutralizing-effective quantity of a chelating agent. By neutralizing, it is intended that the Group IIIa metal will be complexed by a suitable chelating agent such that the complex confers neither beneficial nor detrimental effect on the treated individual. The Group IIIa metal is preferably in the form of a suitable salt, e.g., a nitrate salt. The present sequential administration method may be effected by any suitable means, such as by oral, sublingual, vaginal, rectal, parenteral, or transdermal means. The chelating agent used may be any suitable chelating agent, preferably those able to form a hexadentate complex, such as EDTA, EGTA, CDTA, or DPTA. When the metal is Tl or In, then the chelating agent for stopping the effect is preferably EGTA, CDTA, or DPTA, most preferably CDTA. When the metal is Al or Ga, the chelating agent used to stop the effect is preferably EDTA. The cell-mediated disorders that may be treated by this treatment method include those disorders where the responsible cells have proton pumps in their membrane, such as osteoclasts and macrophages, for example, and that affect calcium metabolism. The disorders for which the present inventive method is useful include osteoporosis, Paget's disease, hypercalcemia, rheumatoid arthritis, metastatic bone disease, and others. Other disorders that are usefully treated by the present invention include immune disorders, such as autoimmunity, that result in local inflammation and bone destruction.

Another embodiment of the present invention is a method for the treatment of a vertebrate animal exposed to a toxic quantity of In-EDTA or Tl-EDTA comprising administering to such a vertebrate animal at least one chelating agent selected from the group consisting of EGTA, CDTA, and DPTA. By administering an effective amount of the aforementioned chelating agents, which inactivate the Group IIIa metals when complexed thereto, one can ameliorate or reverse the ill-effects of an accidental or intentional overdose of the Group IIIa metals, particularly of the present inventive complexes In-EDTA and Tl-EDTA. Effective amounts of the inactivating chelating agents typically are in excess of the quantity of Group IIIa metal composition that was first administered. Suitable excess amounts are two- to ten-fold quantities on a molar basis of the quantity of the administered Group IIIa metal.

The present invention also provides a composition comprising a chelating agent and at least one of the group of metals consisting of In(III) and Tl(III).

Any suitable chelating agent may be used with In and Tl. Such suitable chelating agents include those which, in combination with In and Tl, are effective or ineffective in blocking cellular proton pump activity. If ineffective in blocking cellular proton pump activity, the complex of a chelating agent and In or Tl should have little or no effect on other bodily tissues or functions and be capable of stopping the cellular proton pump effect of those Group IIIa metals. Such chelating agents that are ineffective in combination with Tl or In for blocking the cellular proton pump include EGTA, CDTA, and DPTA. Those suitable chelating agents that, with In or Tl, are effective in blocking cellular proton pump activity, preferably are capable of having at least one of its coordination bonds available to interact with the proton pump, and the remaining coordination bonds available to interact with the metal atom. Further suitable chelating agents preferably are acceptable for pharmaceutical formulations. Such a chelating agent is EDTA. In view of the other chelating agents known to practitioners of the relevant art, it is believed that other chelating agents may be identified that will have at least the equivalent effectiveness as EDTA in combination with In or Tl and that these other chelating agents can be identified without undue experimentation.

Modern coordination chemistry has demonstrated that EDTA-type complexes with metals in the III-designated state are hexadentate except when the ionic radius of the metal is too large to be accommodated by the ligand. For EDTA, this limit is 0.75 angstroms (Douglas and Radanovic, *Coordination Chemistry Reviews*, 128, 139–165, 1993), whereas the ionic radius of Tl[III] is 0.96 angstroms (Blixt et al., *Inorg. Chem.*, 31, 5388–5297 (1992)). When the metal is too large, as it is in the context of the present invention, it forms a sixth ligand with water, other ions, or, in the present case, the proton pump of bone-resorbing cells. A chelator of increased size will form hexadentate complexes that are not inhibitors, even with large metals like Tl[III]. Observations with the inactive EGTA-complex of Tl[III], noted above, are consistent with this analysis. Increasing the number of carboxylate arms of a chelator will also allow the formation of inactive complexes between Tl[III] and such a chelator, as observed for DPTA. Further chelating agents that one familiar with the art would predict to form inhibitory complexes include but are not limited to: (1) agents that have a carboxylate arm missing, such as, for example, ethylenediaminetriacetic acid and similar compounds; (2) agents that have ring structures that prevent the formation of a carboxylate ligand, such as, for example, cyclohexanediaminetetracetic acid; (3) aromatic agents that are too constrained to form a hexadentate complex, such as, for example, xylylenediaminetetraacetate; (4) agents that form an unsymmetrical complexes where geometrical isomers cannot form hexadentate complexes with the IIIa metals, such as, for example, ethylenediamine-N,N,N'-triacetate-N'-propionate or ethylenediamine-N-acetate-N,N',N'-tripropinate; (5) agents that are unsaturated and have restricted geometry, such as, for example, stilbenediaminetetraacetate.

Compounds that one familiar with the art would predict form inactive (i.e., non-inhibiting) complexes include those that form stable hexadentate ligands with group IIIa metals by: lengthening the ethylenediamine group (such as 1,3-propanediamine or 1,4-butanediamine); lengthening the carboxylate arms to 3–5 carbons (such as ethylenediaminetetrapropionic acid); increasing the number of carboxylate arms on the ligand (such as DPTA). These and many similar compounds are available to those familiar in the art who, upon receiving the teaching of the present invention, would recognize the equivalency of the use of these various chelating agents in the context of the present invention.

As recited fully below, the present inventive composition further preferably comprises a pharmaceutical carrier. As such, the present inventive composition is most preferably formulated for oral, sublingual, vaginal, rectal, parenteral, or transdermal administration.

The present invention also provides a composition comprising Ga(III) and one or more of the group consisting of EDTA, EGTA, CDTA and DPTA. Such a composition can form in vivo and is useful in an improvement upon the aforementioned method of administration of free Ga(III) (in the form of gallium nitrate, for example). As such, both beneficial and deleterious effects of Ga(III) can be stopped.

It is surprising that such Group IIIa metals would be useful in the present invention in view of the earlier work on one Group IIIa metal, namely gallium. Used as a nitrate salt, gallium did inhibit bone resorption, but also had various and significant deleterious side-effects that severely limited the usefulness of the gallium compound in this regard. Moreover, compounds that include other Group IIIa metals such as thallium or indium, have been found to be largely insoluble in physiological liquids or physiologically compatible buffers, and thus were considered unlikely to be useful. One of ordinary skill in the art, therefore, would not have expected these Group IIIa metals to be useful for this purpose.

Surprisingly, the complexes comprising In-EDTA and Tl-EDTA are sufficiently soluble in physiological solvents such that they can inhibit vesicle acidification and bone resorption by intact cells in a reliable and repeatable fashion. In particular, therefore, a significant aspect of the present invention is the discovery that complexes of Tl(III) and In(III) metals and a suitable chelating agent can disrupt bone resorption activity by osteoclasts. As indicated, using the metals in the +3 oxidation state is quite effective.

Gallium, another Group IIIa metal, was found to be ineffective when used as a complex with EDTA or EGTA. However, the adverse effects of gallium nitrate treatment for osteoclast inhibition, such as anemia, nausea and vomiting, and renal toxicity, may be reduced or eliminated if such treatment is followed by a subsequent administration of a suitable chelating agent that stops the cellular proton pump effect of gallium, such as EDTA. Aluminum, another Group IIIa metal, is believed to behave similarly to Ga in view of the relative positions of these elements in the periodic table, ionic radius, and their similar solubility characteristics.

The in vivo administration of the metals, chelating agents, complexes, and the like in the context of the present invention may be by any suitable means, including, for example, by oral, sublingual, vaginal, rectal, parenteral, or transdermal means. The contact of cells in vitro with such compounds may be effected using any suitable means that are well known in the art of cell culturing. Any vertebrate animal in need of such treatment may be treated according to the present invention. Preferably, humans and domestic animals are treated according to the present invention. Domestic animals include dogs, cats, horses, cows, chickens, and other companion or work animals associated with humans. More preferably, the present invention is used for treatment of humans, dogs, and horses. Most preferably, the present invention is used for treatment of humans. Cell-mediated disorders include those disorders that affect calcium metabolism or inflammation, such as osteoporosis, Paget's disease, hypercalcemia, rheumatoid arthritis, metastatic bone destruction (or neoplastic bone resorption), and various immune disorders, such as autoimmunity, and others.

The chelating agent-metal complex employed in the present invention may be formulated in any of several pharmaceutically acceptable forms, may be used alone or in appropriate association, and also may be used in combination with other pharmaceutically active compounds. Similarly, the Group IIIa metal when used as a free metal may be formulated in any of several pharmaceutically acceptable forms, such as a salt, may be used alone or in association with appropriate additives, excipients, etc., as described further hereinbelow, and also may be used in combination with other pharmaceutically active compounds. The active agent, whether as a complex or a free metal, may be present in the pharmaceutical composition in any effective quantity. The pharmaceutically acceptable excipients described herein, for example, vehicles, adjuvants, carriers or diluents, are readily known in the art.

While the method of the present invention can be practiced in vitro, as described above to block the proton pump of cultured cells, it has particular usefulness in in vivo applications. The chelating agent-metal complex, whether administered as such or caused to form in vivo, has particular utility in, for example, the treatment of a wide range of disorders. One class of such disorders is associated with calcium metabolism where the bone-resorption activity of osteoclasts is unbalanced relative to osteoblast activity. Such disorders include, but are not limited to, osteoporosis in its various manifestations, Paget's Disease, hypercalcemia, myositis ossificans, and others. Preferably, the present invention provides a method for the treatment of osteoporosis and hypercalcemia.

Other classes of conditions associated with increased bone resorption are the administration of corticosteroids and inflammatory bone destruction in rheumatoid arthritis, other autoimmune diseases and neoplastic destruction of bone. In these situations, there is an increased bone resorption and, perhaps, also a reduction in bone formation. The present invention inhibits the bone removal at both the anatomical and the biochemical site of resorption and therefore has utility even if normal regulatory controls are disturbed. Since the effectiveness of the present invention is closely allied to its tight binding to the bone surface, the present invention is also useful in the treatment of localized inflammation, e.g., rheumatoid arthritis. These situations may be approached with localized intermittent or short term therapy to the site afflicted and therefore would be less prone to the potential complications of extended therapy. The goal of such therapy is a reduction in bone loss so that when the primary disease is controlled, the recovery of the bony tissue will be more rapid.

One skilled in the art will appreciate that suitable methods of administering compounds in the context of the present invention to an animal are available, and, although more than one route can be used to administer a particular active agent, a particular route can provide a more immediate and more effective reaction than another route. Pharmaceutically acceptable excipients are also well-known to those who are skilled in the art, and are readily available. The choice of excipient will be determined in part by the particular complex or free metal, as well as by the particular method used to administer the composition. Accordingly, there is a wide variety of suitable formulations of the pharmaceutical composition of the present invention. The following methods and excipients are merely exemplary and are in no way limiting.

Formulations suitable for oral administration can consist of (a) liquid solutions, such as an effective amount of the complex dissolved in diluents, such as water, saline, or orange juice; (b) capsules, or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, stearic acid, and other excipients, colorants, diluents, buffering agents, moistening agents, preservatives, flavoring agents, and pharmacologically compatible excipients. Lozenge forms can comprise the active ingredient with a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The active agents of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the complex employed in the present invention may be made into suppositories by mixing with a variety of bases such as emulsifying bases or water-soluble bases.

Formulations suitable for vaginal administration may be presented as pessaries, tampons, creams, gels, pastes, foams, or spray formulas containing, in addition to the active ingredient, such carriers as are known in the art to be appropriate.

The dose administered to an animal, particularly a human, in the context of the present invention should be sufficient to effect a prophylactic or therapeutic response in the animal over a reasonable time frame. One skilled in the art will recognize that dosage will depend upon a variety of factors, including the strength of the particular compound employed, the condition of the animal, the body weight of the animal, as well as the severity and stage of the condition or disorder being treated. The size of the dose will also be determined by the existence, nature, and extent of any adverse side-effects that might accompany the administration of a particular compound. Specifically, a suitable dose is that which will result in a concentration of the active agent at bone tissue that is known to impair or block the bone dissolution activity of osteoclasts, e.g., from about $1\times10^{-8}$ to about $2\times10^{-5}$ mole/kg body weight, i.e., from about 0.005 mg to about 10 mg per kg body weight. The preferred dosage is the amount that results in diminution of bone dissolution and/or above-normal serum calcium levels, without significant side effects. For example, Tl and EDTA can be mixed in a 3:5 ratio (e.g., 30 millimolar+50 millimolar) to render a colorless solution. The pH of the solution can then be raised to 7.0, filtered to achieve sterility, and used for intravenous administration. Such a solution may be administered in dosages of from about 0.25 µl to about 700 µl per kg body weight. Preferred dosages of the solution are from about 1 µl to about 250 µl per kg body weight; more preferred dosages of the solution are from about 10 µl to about 100 µl per kg body weight. Tabular formulations and dosages thereof for oral administration may be provided using methods well known in the art.

The desirable extent of the inhibition of bone-resorbing activity of osteoclasts or the inflammation-causing activity of macrophages will depend on the particular condition or disorder being treated, as well as the stability of the patient and possible side-effects. In proper doses and with suitable administration of certain compounds, the present invention provides for a wide range of the inhibition of bone-resorbing activity or inflammation-causing activity, e.g., from little inhibition to essentially full inhibition, including providing an antidote to toxic levels of Group IIIa metals.

The following examples further illustrate the present invention and, of course, should not be construed as in any way limiting its scope.

EXAMPLE 1

This example illustrates the increased solubility of certain Group IIIa metals when complexed by a sequestering agent as compared to the respective free salt forms.

Complexes of Tl and In with EDTA were prepared as follows: Tl and EDTA were mixed in a 3:5 ratio to prepare various mM concentrations of Tl-EDTA in physiological saline. The pH of the resulting solutions was then raised to pH 7.0 and filtered to achieve sterility. In-EDTA was prepared in a precisely analogous manner. The solubility characteristics of these Tl and In complexes were compared to the solubility characteristics of the respective halogen salts. Solutions of at least 50 to 100 mM Tl-EDTA or In-EDTA were prepared in physiological saline. By contrast, millimolar concentrations of $TlCl_3$ or $InCl_3$ could not be prepared in the same buffer. Moreover, the uncomplexed halide salts readily precipitated from solution and/or displayed changes in color that were consistent with valence changes.

EXAMPLE 2

This example illustrates that the Tl-EDTA and In-EDTA complexes are each effective inhibitors of osteoclast-mediated bone resorption in vitro.

Osteoclasts were isolated from calcium-deprived, laying hens, and metabolically radiolabelled bone was prepared therefrom (Blair et al., *J. Cell Biol.*, 102, 1164–1172 (1986)). These osteoclasts were cultured in 24 well dishes at 10,000 cells per well, to which were added labelled bone and test compounds. The culture supernatants were assayed for released radioactivity for up to six days after the addition of the labelled bone.

Figure 2:
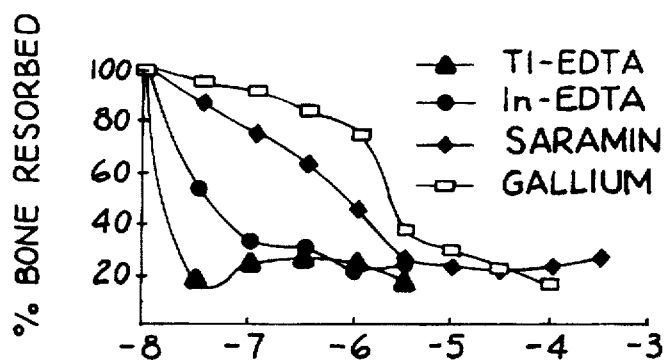
FIG. 2 is a graph that presents the observed results of inhibition of bone resorption activity of osteoclasts in culture in response to various test compositions.

FIG. 2 shows the extent of inhibition of bone resorption by osteoclasts in culture in response to various concentrations of control compositions and the compositions of the present invention. The y-axis indicates the percentage of the total radiolabelled bone that was released by osteoclast activity to the culture supernatant in response to varying the molar concentration (x-axis) of the various test compositions. The present inventive compositions Tl-EDTA and In-EDTA were very effective inhibitors of osteoclast activity. The 50% effective concentration of the Tl-EDTA and In-EDTA complexes were <10 nM and 30 nM, respectively. In contrast, suramin and gallium nitrate were tested in the absence of a chelating agent and were found to be significantly less effective. The 50% effective concentrations of suramin and gallium nitrate were 700 nM and 2000 nM, respectively.

EXAMPLE 3

This example illustrates the effect of the metal-EDTA complexes on the enzymatic activity of the osteoclast membrane proton pump.

The effect of the metal-EDTA complexes on the proton pump of isolated osteoclast ruffled membrane vesicles was studied. For the study, the isolation, preparation and assay of the acidifying ruffled membrane vesicles were accomplished according to the procedures of Blair et al., *J. Cell. Biochem.*, 48, 401–410 (1992).

Figure 3:
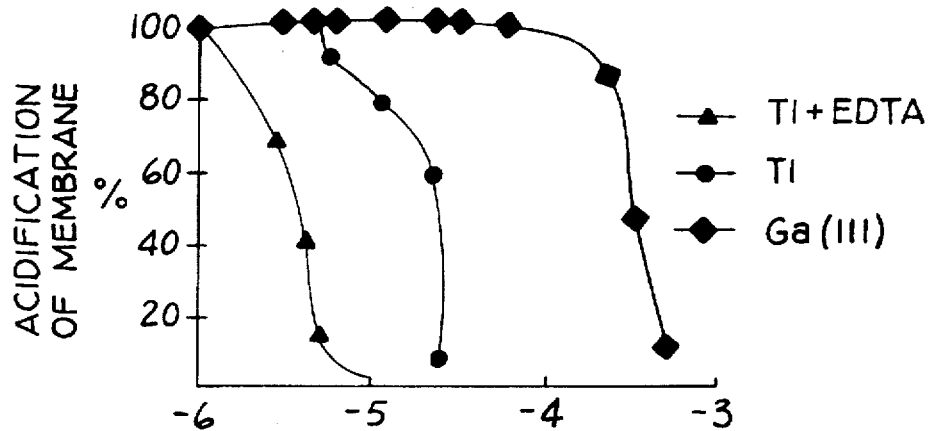
FIG. 3 is a graph that presents the observed effects of the test compositions on the proton pump of the osteoclast ruffled membrane vesicles.

FIG. 3 presents the observed effects of the test compositions on the proton pump of the osteoclast ruffled membrane vesicles. The y-axis indicates the acidification by the membranes in relation to the molar concentration of the test composition, as indicated on the x-axis. The acidification of the osteoclast ruffled membrane vesicles was clearly inhibited, as noted in FIG. 3, but at concentrations significantly higher than those that inhibited bone resorption. The 50% effective concentrations for Tl-EDTA, Tl alone, and Ga alone were 3 µM, 30 µM, and 300 µM, respectively.

Because both the chloride channel and the proton pump are present in the ruffled membrane vesicles, the inhibition of acidification that was observed was possibly due to effects on either or both of these transporters. The effects of these two transporters were distinguished in other experiments by noting and using the differential effects of valinomycin on the chloride channel and proton pump in the presence of 120 mM $K^+$. This drug relieves the build-up of membrane potential yet permits proton transport. Control measurements verified that when the chloride channel was inhibited, using methods known in the art, the acidification was severely restricted but recovered when 1 micromolar valinomycin was added. Another control measurement showed that direct inhibition of the proton pump, using methods known in the art, was not reversible by the addition of valinomycin. In the test measurement, it was found that the inhibition by metal-EDTA complexes was not reversed by the addition of valinomycin, which is consistent with the conclusion that the Tl-EDTA and In-EDTA complexes predominantly affect the proton pump.

EXAMPLE 4

This example illustrates that the Tl-EDTA and In-EDTA complexes are each effective inhibitors of osteoclast-mediated bone resorption in vivo.

Figure 4:
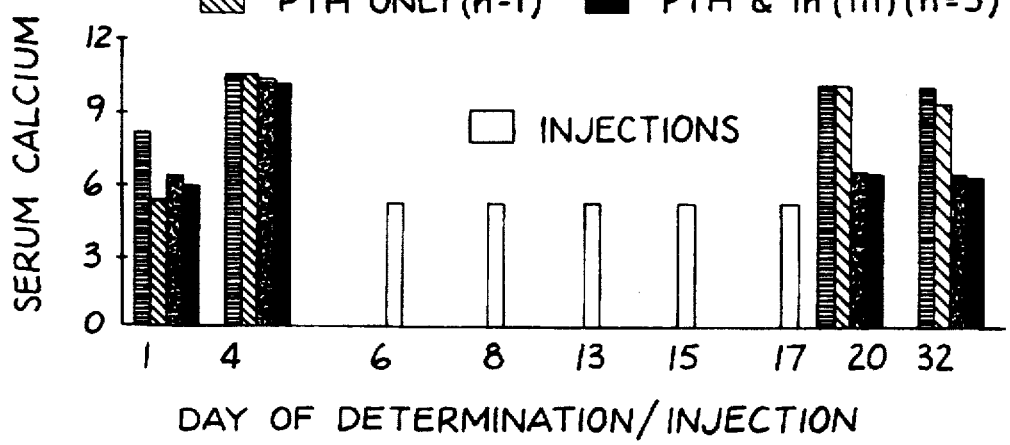
FIG. 4 is a bar graph that presents the observed results of an experiment directed to the in vivo activity of metal-EDTA complexes on the parathyroid hormone stimulated bone resorption of rats.

The ability of the metal-EDTA complexes to inhibit osteoclast-mediated bone resorption was tested on two groups of experimental rats treated to provide a hypercalcemia model (according to the procedures of Jaeger et al., *Am. J. Physiol.*, 252, E790–E798 (1987)) as compared to two groups of untreated control rats. Experimental rats were surgically parathyroidectomized, and the effectiveness of the parathyroidectomy was gauged by determining the subject rats' serum calcium levels 72 hours post-surgery. A fall in calcium observed at that time reflected the decrease of bone resorption resulting from the removal of the parathyroid glands and the consequent decrease in circulating parathyroid hormone (PTH), a regulator of extra-cellular $Ca^{++}$ concentration. A second surgery was then performed to implant subcutaneous osmotic pumps that administered a constant dosage of synthetic PTH (BPTH 1–34 (i.e., rat peptide 1–34), purchased from Bachem California, Torrence, Calif.; Jaeger et al., *Am. J. Physiol.*, 252, E790–E798, 1987)), which was maintained throughout the experiment. The dose was adjusted so that, as shown in FIG. 4 (described in detail below), the experimental rats increased their serum calcium to 150% of the pretreatment levels, which constituted a mild hypercalcemic condition and reflected increased bone resorption. The animals were followed to establish a baseline and then, after 7 days, given injections of 10 micromole of Tl-EDTA or In-EDTA complex per kilogram of body weight every third day for two weeks. Serum calcium levels were determined after a 24-hour fast on the third day after the last drug administration and again two weeks later.

All the animals in this study underwent the same two surgical procedures and received PTH via the implanted osmotic pump starting on day 3. The control animals were not given the metal complexes and three did not have their parathyroid glands removed (having undergone sham operations only). There was also one animal that had its parathyroid removed but was not administered the metal complexes. The remaining animals were treated identically as experimental animals: Tl-EDTA (n=3) or In-EDTA (n=3) was administered on an every third day schedule for two weeks. After the two weeks were complete, serum calcium was determined again and compared to the earlier values and the controls. The animals that received PTH and not Tl-EDTA or In-EDTA were observed to have elevated calcium concentrations whether or not the parathyroid gland was removed. This result indicated that the PTH was pharmacologic and stimulated bone resorption even in normal animals.

The results of this experiment are set forth in the bar graph of FIG. 4. The y-axis indicates the serum calcium levels in mg/dl units. The x-axis indicates the day of the various serum calcium determinations or the day of injections of the test compositions. On Day 1, Day 4, Day 20, and Day 32, four bars indicating the results of serum calcium assays on each of the two control and two experimental groups of animals are presented. Starting from the left, each group of bars represents the serum calcium concentrations for (1) the control group of rats that received no test composition, (2) the control rat that received PTH only, (3) the experimental group of rats that received Tl-EDTA plus PTH, and (4) the experimental group of rats that received In-EDTA plus PTH, respectively. Injections are indicated by the open bars on Day 6, Day 8, Day 13, Day 15, and Day 17.

As can be seen in FIG. 4, by Day 4, all pumps were working and had successfully caused the serum calcium level of the experimental rats to be elevated to a mild hypercalcemic condition, that being about 10 mg/dl for all groups of experimental rats. On Day 20, those rats that received the metal-EDTA complex had normal, pretreatment levels of serum calcium. Thus, the animals treated with metal complexes had a lowered serum calcium concentration that persisted for at least two weeks after the last administration of the complex.

EXAMPLE 5

This example illustrates the use of Tl-EDTA to counteract the loss of bone mass in rats that have had their ovaries surgically removed by an oophorectomy.

The ovaries are the primary source of estrogen in female mammals, and their loss results in imbalanced bone metabolism similar to the experience of postmenopausal females. Twenty-eight rats (female, 250 grams) were surgically oophorectomized (all survived) on day 1 of the study and then groups of animals were treated in several ways. Fourteen oophorectomized animals were injected every third day with 10 μmole/kilogram of Tl-EDTA in sterile isotonic saline, the remaining 14 were injected with 10 μmole EDTA in isotonic saline. Twelve animals underwent "sham" surgery in which all of the surgical steps were performed, except for the removal of the ovaries. Six of these animals received 10 μmole/kilogram Tl-EDTA in isotonic saline, and six received 10 μmole/kilogram of EDTA in isotonic saline. All injections were intraperitoneal and in total volumes of 0.08–0.120 ml.

Figure 5:
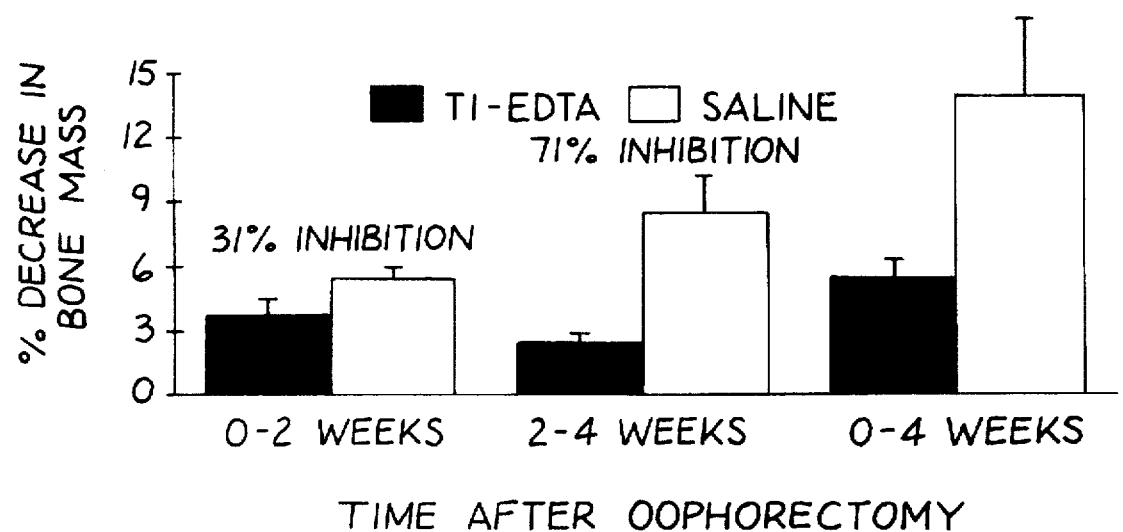
FIG. 5 is a bar graph that presents the observed results of an in vivo administration of the metal-EDTA complexes on the excessive resorption of bone by oophorectomized rats.

At the beginning of the study, on day 14, and on day 28, bone mass of each animal was estimated densitometrically using a Hololgic QDR(1000) bone densitometer, applying previously reported methods (Rupich et al., *J. Bone Miner. Res.*, 7, 97–100 (1992)). The results were analyzed in a standard manner (Rupich et al., supra) and are set forth in FIG. 5 as percent bone loss, with the bone density at time 0 being set at 0 percent bone loss. Errors were computed as standard deviations in the usual manner and are present as error bars in FIG. 5. After two weeks, the administration of Tl-EDTA and the saline solutions was discontinued. The results showed in the untreated animals following oophorectomy that there was a bone loss of 15% measured after 4 weeks and that the Tl-EDTA administration reduced that bone loss by 61%. Furthermore, there was no decrease in the inhibition of bone loss during the second 2-week period, when the agent was not administered, thereby indicating significant persistence of effect. Finally, the animals that received a "sham operation" showed some bone loss, which is probably related to the surgical trauma. Although this bone loss was small, the sham-operated animals' bone loss was reversed as well by Tl-EDTA. Therefore, Tl-EDTA was effective in reversing bone loss due to estrogen deficient states (similar to those which occur in menopause-related osteoporosis). Tl-EDTA was also effective in reversing bone loss that was secondary to stress, as in the sham operated animals (a condition that is more closely related to the effect of increased levels of corticosteroids).

The contents of each of the references identified herein are hereby incorporated by reference in their entirety.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for blocking a cellular proton pump that comprises contacting a cell with a cellular proton pump-blocking-effective quantity of In-EDTA or Tl-EDTA.

2. The method of claim 1, wherein said contacting is effected in vitro.

3. The method of claim 1, wherein said contacting is effected in vivo by administering said composition to a vertebrate animal.

4. The method of claim 1, wherein said cell is an osteoclast or a macrophage.

5. The method of claim 1, wherein said method further comprises a subsequent contact of said cell with a chelating agent that stops the cellular proton pump-blocking-effect of said In-EDTA or Tl-EDTA.

6. The method of claim 5, wherein said chelating agent is selected from the group consisting of EGTA, CDTA, and DPTA.

7. A method for sequentially blocking and unblocking a cellular proton pump that comprises contacting a cell with a cellular proton pump-blocking-effective quantity of a Group IIIa metal followed by contacting said cell with a sequestering-effective quantity of a chelating agent that stops said cellular proton pump-blocking effect.

8. The method of claim 7, wherein said sequential contacting is effected in vitro.

9. The method of claim 7, wherein said sequential contacting is effected in vivo.

10. The method of claim 7, wherein said chelating agent is selected from the group consisting of EGTA, CDTA, and DPTA.

11. The method of claim 7, wherein said metal is Ga or Al and said chelating agent is EDTA.

12. The method of claim 7, wherein said cell is an osteoclast or a macrophage.

\* \* \* \* \*

UNITED STATES PATENT AND TRADEMARK OFFICE
CERTIFICATE OF CORRECTION

PATENT NO. : 5,763,480

DATED : June 9, 1998

INVENTOR(S) : Paul H. Schlesinger, et. al.

It is certified that error appears in the above-identified patent and that said Letters Patent is hereby corrected as shown below:

Title page, item [54] and col. 1, line 1, should read – INHIBITORS OF CELL-MEDIATED DISORDERS --.

Signed and Sealed this

Twenty-sixth Day of January, 1999

Attest:

Attesting Officer

*Acting Commissioner of Patents and Trademarks*